United States Patent [19]

Tomasovic et al.

[11] Patent Number: 4,639,306

[45] Date of Patent: Jan. 27, 1987

[54] ELECTROCHEMICAL GAS SENSOR

[75] Inventors: Beth A. Tomasovic, New Kensington; Robert L. Novack, Evans City, both of Pa.

[73] Assignee: Bacharach, Inc., Pittsburgh, Pa.

[21] Appl. No.: 777,989

[22] Filed: Sep. 20, 1985

[51] Int. Cl.[4] .................. G01N 27/30; G01N 27/46
[52] U.S. Cl. .................................................. 204/432
[58] Field of Search .............. 204/432, 1 F, 411, 412, 204/415, 431

[56] References Cited

U.S. PATENT DOCUMENTS

| 3,634,569 | 1/1972 | Emanuelson et al. | 264/105 |
|---|---|---|---|
| 3,801,374 | 4/1974 | Dews et al. | 136/120 |
| 3,859,138 | 1/1975 | Narsavage et al. | 136/120 |
| 3,912,538 | 10/1975 | Dews et al. | 136/86 D |
| 3,992,331 | 11/1976 | Petrow et al. | 252/472 |
| 4,001,103 | 1/1977 | Blurton et al. | 204/411 |
| 4,028,274 | 6/1977 | Kunz | 252/447 |
| 4,044,193 | 8/1977 | Petrow et al. | 429/40 |
| 4,127,462 | 11/1978 | Blurton et al. | 204/195 R |
| 4,167,457 | 9/1979 | Giner | 204/432 X |
| 4,313,972 | 2/1982 | Goller et al. | 427/113 |

Primary Examiner—G. L. Kaplan
Attorney, Agent, or Firm—Webb, Burden, Robinson & Webb

[57] ABSTRACT

An apparatus for the detection and measurement of an object gas is disclosed. Such an apparatus comprises a sensing electrode having a catalytic surface, a counter electrode having a catalytic surface, an electrolyte in electrical contact with the sensing electrode and the counter electrode, a reference electrode in contact with the electrolyte and the sensing electrode, a means for supplying an electrical potential between the sensing electrode and the reference electrode and a means for measuring the current flow resulting from the reaction of the object gas with the sensing electrode by way of the sensing electrode substrate to the counter electrode substrate. The substrate, which supports the catalytic sensing electrode and counter electrode materials being electrically conductive carbon or graphite, which allows the electrons generated at the sensing electrode catalytic surface to be removed through the substrate instead of from the surface.

3 Claims, 2 Drawing Figures

ELECTROCHEMICAL GAS SENSOR

TECHNICAL FIELD

The technical field to which this invention pertains is electrochemical gas detectors, in particular, those detectors useful for detecting noxious or dangerous gases.

BACKGROUND ART

Electrochemical cells and electrolyte reactions have been used extensively to detect particular gases such as oxygen, carbon monoxide, carbon dioxide, etc. Typically, these cells comprise an anode, a cathode, in electrical contact with one another having an electrolyte dispersed between and in contact with each of the electrodes. The cell responds to an object gas which comes in contact with one of the electrodes at the interface of a catalytic surface of the electrode and the electrolyte. The object gas is either oxidized or reduced resulting in the production of electrons. These electrons are then conducted across the catalytic face of the electrode to a collector plate where they are then carried by means of a wire across to the second electrode. The resulting current flow is a measure of the amount of object gas present in the sample.

The electrodes used in the traditional electrochemical gas detection cells are comprised of a hydrophobic, electrically nonconductive support with an electrically conductive, catalytic face in contact with the electrolyte. As the object gas is introduced into the detector, it passes through the porous electrode substrate of the sensing electrode and eventually contacts the catalytic/electrolyte interface. At this interface the object gas undergoes an oxidation/reduction reaction which produces electrons and ions. The electrons are then collected from the sensing electrode (anode or cathode) and conducted through an electrically conductive wire to the counter electrode where a second and opposite reaction takes place. The measure of the current flow between these electrodes is representative of the amount of the detectable gas in the object gas.

These conventional electrode designs produce a number of disadvantages. First, the electrodes have an electrically, nonconductive, hydrophobic substrate. This requires that the conduction of electrons resulting from the catalytic reaction, be collected from the catalytic surface of the sensing electrode. This requires the placement of a collector plate or grid on the catalytic surface of the electrode and in electrical contact with the catalyst surface. In such a configuration, these collector plates or grids are in constant contact with the electrolyte, which is typically highly corrosive. Therefore, these collector plates must be made from corrosive resistant materials, in many instances these materials are exotic and expensive such as tantalum, platinum and gold, adding considerable cost to the entire unit. Additionally, since these collector plates are small, all of the electrons produced at the surface of the electrode must be conducted to it. Therefore, the entire catalytic surface of the electrode must form an electrically conductive continuum. This is only achieved by placing sufficient catalyst material on the surface of the electrode to ensure point to point contact of the catalytic particles. This may require the application of excess catalytic material over the surface to form an effective electrode, just to make sure that the electrical continuity is achieved. Again, this adds additional cost to these detector units.

Yet another disadvantage to these electrodes, is that since the collector plates are placed on the catalytic surface/electrolyte interface, the wires used in conducting the current generated at one electrode to the second electrode, requires that the wires enter and exit the electrolyte cavity. This means that the electrolyte cavity cannot be completely sealed and that there is always a possibility of leakage of the electrolyte at the entrance and exit points of these wires. This leakage, of course, would be disasterous to the operation of the detector.

For these reasons, a new approach is required for designing electrodes specifically for these gas detector units. What is needed is an electrode which does not require electrical continuity across its catalytic face, so that the electrical current can be removed without having the collector plates or electrical wires inside the electrolyte cavity. This would allow designers of these detector units greater flexibility, and potentially produce a gas detector at a lower cost.

DISCLOSURE OF INVENTION

The present invention discloses a portable apparatus for the detection of a gaseous component in an object gas in which the apparatus contains an anode, a cathode, either of which may act as the sensing electrode while the other acts as the counter electrode, an electrolyte in electrical contact with said anode and cathode, a reference electrode in contact with the electrolyte and the sensing electrode, a means for supplying and maintaining an electrical potential between the sensing electrode and the reference electrode and a means for measuring the current flow from the sensing electrode to the counter electrode. In this invention, unlike those of the prior art, both the anode and the cathode electrodes have a catalytic surface which is in contact with the electrolyte and which is supported on an electrically conductive substrate. This electrically conductive substrate allows the current flow between the anode and the cathode to take place between these two substrates, therefore eliminating the need for collector plates to be in contact with the catalytic surface of each electrode.

Other features and advantages will be apparent from the specification and claims and from the accompanying drawings which illustrate an embodiment of the invention.

BEST MODE FOR CARRYING OUT THE INVENTION

Figure 1:
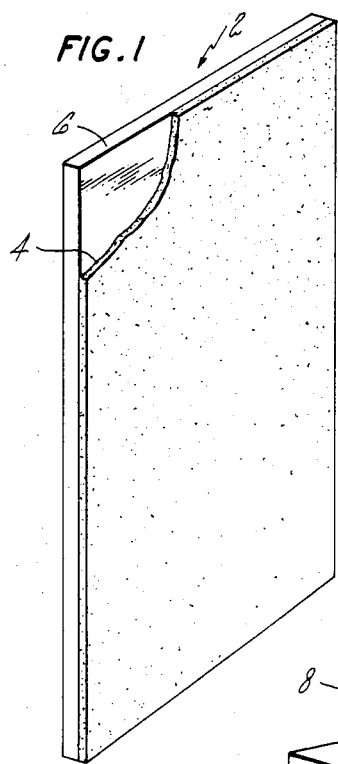
FIG. 1 is an illustration of the conventional electrodes.

The electrode substrates useful in this invention will typically be comprised of carbon or graphite particles pressed to form a porous, electrically conductive paper substrate. These paper substrates may be formed in the same manner as those prepared for fuel cell technology. A number of different procedures may be used, a few of which are described in U.S. Pat. Nos. 3,388,004; 3,992,331; 4,044,193 and 4,166,143, the contents of which are incorporated herein by reference. These substrates must possess two physical characteristics. One, they must be porous to the object gas to be measured, thereby allowing the object gas to pass from the electrode substrate side to the catalytic surface where it is reacted at the catalyst/electrolyte interface. Secondly, the substrate of the catalyst must be electrically conductive, but not electrochemically active, i.e., inert, to allow a flow of electrons from the catalytic reaction occurring at the catalytic/electrolyte interface through the electrode to a collector plate situated on the noncatalytic side of the electrode substrate. This is in direct contrast to the prior art method (as shown in FIG. 1) which removes the electrons generated at the catalytic/electrolyte interface using a collector plate 3 and a wire 5 in contact with the catalytic surface 4.

These substrates are typically carbon papers made by carbonizing a fiber such as nylon or rayon by heating it to about 1300° F. (704.4° C.) to about 1500° F. (815.5° C.). The carbonized fibers may then be cut to the desired length and made into paper by any one of the well known paper making processes. These papers may be graphitized by further heating. Although it is not necessary, it may be preferred that these carbon papers be made hydrophobic through the impregnation of a hydrophobic material such as a polyfluorinated polymer such as Teflon ® polymers. The impregnation process is conventional and should be performed such that the electrical properties associated with the graphite substrate are not markedly reduced.

The preferred carbon substrates should be comprised of carbon or graphite containing about 30 percent to about 50 percent by weight of Teflon ® polymers, preferably about 38 percent by weight. It has been found that too little Teflon will result in a substrate having insufficient hydrophobicity, while too high a content will produce an unacceptably high electrical resistance in the substrate.

The preferred paper substrate will be about 5 mils to about 20 mils thick with substrates having thicknesses of about 12 to about 15 mils being preferred. These substrates may further be characterized as having electrical conductivities of above 10 ohm$^{-1}$ cm$^{-1}$ and a porosity of above 10%.

Although these substrates have been described as preferably being made of carbon or graphite, this disclosure should not be so limited. These conductive substrates may also be made of fibrous carbon felt, porous rigid carbon boards, or any of the conductive polymeric materials, such as polyacetylene, which would be compatible with the electrolyte and not be detrimental to the electrochemistry, and possess the electrical properties and porosity required of these gas detectors.

Once the electrically conductive substrate has been prepared, a conventional catalytic surface is applied to the surface of the substrate which will be in contact with the electrolyte. These catalytic materials will be those conventional in the art of gas analyzers and will be chosen to be responsive to the particular gas or gases to be detected. Typically, these will be oxides or pure metals from the precious metal groups of the periodic table, some of which will include gold, gold oxide, platinum, palladium, rhodium, iridium, silver, etc. and even some of the transition metals such as iron, cobalt or nickel, etc. These catalysts can be applied to the substrate in conventional procedures. Typically, the catalyst is formed into an aqueous slurry containing about 1% to about 60% by weight of the catalyst, and is then placed onto the electrode substrate with a spatula or roller or other technique which will apply it uniformly to the surface of the substrate. Typically, the catalyst layer will be about 1 to about 5 mils in thickness with a preferred range of about 2 mils to about 3 mils. In a preferred method for preparing these catalysts, the aqueous slurry which contains the catalytic material is often mixed with a hydrophobic material such as DuPont No. 30 TFE available from the DuPont Corporation, Wilmington, Del. The slurry is mixed thoroughly to ensure satisfactory homogeneity and then applied to the electrode surface as described above and in the same thicknesses. Typically, these catalytic layers will comprise from about 75 to about 15 percent by weight of Teflon ® hydrophobic material, however, this will vary depending on the particular catalyst and analysis to be performed as will the other parameters related to the catalyst, i.e., type used or concentration.

Once the catalyst has been placed on the paper, the structure is placed in an oven and sinter bonded. Typically this is done at temperatures of about 527° F. (275° C.) to about 617° F. (325° C.) for about 15 minutes to about 1 hour. The sintering procedure causes the Teflon polymer in the catalytic layer to bond or fuse with the Teflon polymer of the substrate to securely bond the catalytic layer to the substrate.

Since the substrate in these electrodes is electrically conductive, there is no need to have each catalytic particle in electrical contact with every other catalytic particle forming an electrically continuous surface to conduct the current along its face to the collector plate or grid, as in the prior art. This will allow for lower catalytic loadings and more efficient and cost effective electrodes. It is also possible to dilute a conducting catalyst or to use a nonconductive catalyst by supporting it on finely divided carbon or a combination of a conducting and nonconducting catalyst on the electrically conductive support.

Figure 2:
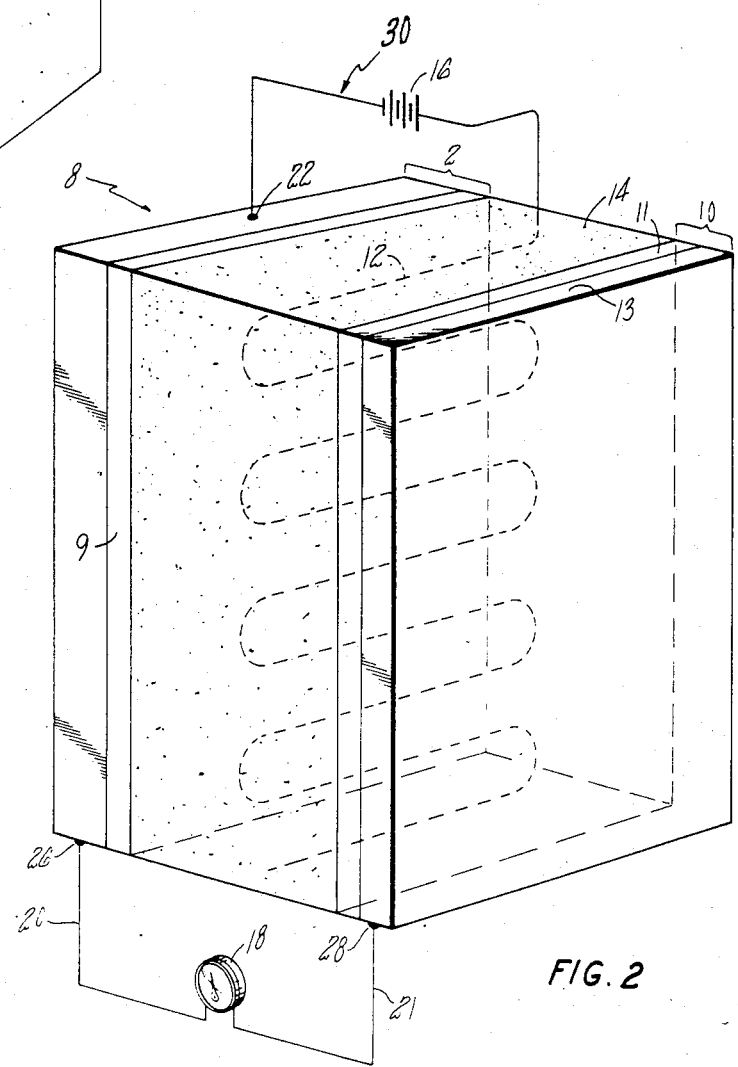
FIG. 2 is an illustration of the electrode of the present invention.

As is shown in FIG. 2, (which is meant to be exemplary and not limiting), these electrodes are then placed in a gas detector cell 8 comprising two electrodes, a sensing electrode 2 and a counter electrode 10, having an electrolyte 14 dispersed between and in contact with each electrode. The electrode should be positioned such that the catalytic surface 9, 11 is facing and in contact with the electrolyte 14. It may be desirable to also include a reference electrode 12 which is in electrical contact with the sensing electrode and wherein an electrical potential is impressed and maintained by means of a power source 16 and connecting wires 30, on the sensing electrode and such potential is maintained constant throughout the analysis. A specific reference electrode which may be used is the air reference electrode and would be known to one skilled in the art. The electrolyte 14 used in these gas detector cells may be any of the standard aqueous or polymeric electrolyte materials used in the prior art gas analysis cells of this type as well as non-aqueous electrolytes. Some of these electrolyte materials which may prove useful are sulfuric acid, phosphoric acid, ion exchange membranes, and propylene carbonate with lithium perchlorate and the like. The operating potential which is impressed on the sensing electrode will be a function of the reaction which takes place at the sensing electrode, the counter electrode and the reference electrode and again would be conventional. In addition, the sensing electrode and counter electrode of the cell will be in electrical contact with one another through wires 20, 21, thereby allowing the electrons generated at the sensing electrode to travel to the counter electrode. The quantity of electrons which flow along the path is measured by meter 18 and is a measure of the amount of object gas present in the sample. The key feature of this gas analysis instrument is the fact that the electrical contact 22 between the sensing electrode and the reference electrode, as well as the electrical contacts 26, 28 between the sensing electrode and the counter electrode, through which the electrons are able to pass in order for the cell to function, are made on the electrically conductive substrates of the electrodes themselves. Heretofore, these contacts had to be made on the catalytic surface of each electrode thereby removing any opportunity by the designer in preventing electrical wires from invading the electrolyte cavity. The reference electrode could also be of similar design to the anode and cathode and avoid a feed through wire contact. However, as can be seen in FIG. 2, these gas cells utilizing these electrodes having electrically conductive substrates allow for the design of a cell having a completely sealed electrolyte cavity, thereby reducing the likelihood of electrolyte leakage and destruction of the cell and related equipment or harm to personnel. In addition, such a design would eliminate the need for the use of exotic metals to act as collector plates on these electrodes due to the fact that the collector plates will not be in contact with the corrosive or possibly corrosive electrolyte material.

It should be understood that the invention is not limited to the particular embodiments shown and described herein, but that various changes and modifications may be made without departing from the spirit and scope of this novel concept as defined by the following claims.

I claim:
1. An apparatus for the detection and measurement of a gaseous component in an object gas comprising:
   a sensing electrode having a porous, electrically conductive substrate with a catalyst dispersed on one or more surfaces,
   a counter electrode having a porous, electrically conductive substrate with a catalyst dispersed on one or more surfaces,
   an electrolyte in contact with the catalytic surface of the sensing electrode and the catalytic surface of the counter electrode,
   a reference electrode in contact with the electrolyte,
   a means for supplying and maintaining an electrical potential between the sensing electrode substrate and the reference electrode, and
   a means for measuring the current flow from the sensing electrode substrate to the counter electrode substrate resulting from the catalytic reaction of the gaseous component at the interface of the sensing electrode and the electrolyte, wherein said electrically conductive substrates have an electrical conductivity greater than 10 $ohm^{-1}cm^{-1}$ and a porosity greater than 10 percent.
2. The apparatus of claim 1 wherein the electrode substrates are hydrophobic.
3. The apparatus of claim 2 wherein the catalytic layer is hydrophobic.

* * * * *